United States Patent [19]

Nebenzahl

[11] Patent Number: 5,125,417

[45] Date of Patent: Jun. 30, 1992

[54] PHASE CONJUGATE REFLECTION FROM PLASMA

[76] Inventor: Isaiah Nebenzahl, 14 Beruria Street, Jerusalem, Israel

[21] Appl. No.: 214,553

[22] Filed: Jun. 29, 1988

[51] Int. Cl.⁵ .............................................. A61N 5/00
[52] U.S. Cl. ................................ 128/804; 330/1 R; 330/43
[58] Field of Search .................. 128/630, 653, 804; 330/1 R, 43

[56] References Cited

U.S. PATENT DOCUMENTS

| | | | |
|---|---|---|---|
| 4,379,998 | 4/1983 | Shockley | 357/26 |
| 4,389,593 | 6/1983 | DeSantis et al. | 315/4 |
| 4,734,911 | 3/1988 | Bruesselbach | 372/99 |
| 4,846,575 | 7/1989 | Lisson | 356/363 |
| 4,887,905 | 12/1989 | Lisson et al. | 356/363 |
| 4,958,908 | 9/1990 | Rockwell et al. | 350/311 |
| 4,977,562 | 12/1990 | Welch et al. | 372/95 |

OTHER PUBLICATIONS

Cheung, A. Y, "Microwave and RF Techniques for Clinical Hyperthermia", Br. J. Cancer (1982) 45, Suppl. V., 16.

Primary Examiner—Francis Jaworski
Attorney, Agent, or Firm—Browdy and Neimark

[57] ABSTRACT

A process and device for generating conjugated micrometer to radio frequency range electromagnetic waves and for their amplification. The conjugated waves are generated by establishing in a plasma two waves of the desired frequency, essentially identical in wavelength at in opposite directions and by directing a third electromagnetic wave of essentially the same frequency so that this will enter the plasma at a predetermined wavelength, resulting in a fourth conjugated electromagnetic wave.

A high magnification of the intensity of the conjugated wave can be attained. Such conjugated waves can be used in human medicine for concentrating waves at a tumor site. Devices of the invention can be used for the intensification of other waves, such as radar frequency waves.

18 Claims, 1 Drawing Sheet

PHASE CONJUGATE REFLECTION FROM PLASMA

FIELD OF THE INVENTION

The invention comprises a method and means for generating a conjugated wave in the range of millimeter waves, microwaves and far infrared waves. The conjugation is effected by a plasma. The invention also relates to the use of the conjugated waves in various fields of technical and medical applications.

BACKGROUND OF THE INVENTION

A conducting medium, such as a metal, a semiconductor, or a plasma, reflects electromagnetic waves impinging on its surface, as is attested for by the shiny appearance of metals. This well-known phenomenon is due to currents induced in the conducting medium by the incoming wave, and the emission of an outgoing wave by these currents acting as an antenna.

Under special circumstances, a different kind of reflection can occur, namely phase-conjugate reflection (R. Fisher, editor: Optical Phase Conjugation. Academic Press 1983. B. Ya. Zeldowich, N. F. Filipetsky and V. V. Shkunov: Principles Of Phase Conjugation. Springer 1985). Whereas regular reflection preserves the phase of the incoming wave, up to a costant $\pi$, phase conjugated reflection inverts it. As a result, regular reflection obeys Snell's Law: the perpendicular to the reflecting surface bisects the angle between the incoming and the outgoing rays. In phase-conjugate reflection, on the other hand, the outgoing ray retraces the incoming ray in reverse, i.e. returns toward the radiation source. When several rays emanating from a point impinge on a conventional reflector, they are so reflected as to further diverge; a phase conjugate reflector converges the rays back to their origin.

These phenomena are by now well established in the field of optics, where special materials have been developed, which serve as phase conjugate reflectors for visible and infrared light. The present invention provides means for phase conjugate reflection of far infrared, microwaves and millimeter waves, i.e. a range where this phenomenon has not been established before. In particular, it is shown that plasma, either in the form of high density of charge carriers in crystals, or in high temperature ionized gases, can be utilized to construct phase conjugate reflectors for electromagnetic fields in these regimes. The reflection of these waves can also be amplified in intensity, as is described below. As a result, it is possible to construct a radiation source similar to the laser, namely of high intensity, coherence and directionality, in the above mentioned regimes.

Several possible fields of application are described for this device, which will hereafter be called plasma phase conjugate reflector, or PPCR.

STATE OF THE PRIOR ART

As described in the above mentioned books of Fisher and of Zeldowich et al., phase conjugate reflection is already an established art. This applies only to the optical and near infrared regimes of the electomagnetic spectrum, i.e. for the wavelengths of 0.3 to 1.0 micrometers. The known materials used to achieve phase conjugate reflection are specially chosen or designed for this range of wavelengths, which is of interest because it is that where most lasers work.

The present invention is the first effort to achieve phase conjugate reflection in the regime of wavelengths from 10 micrometers to 10 centimeters. The materials needed and the methods used are of completely different type than in the optical regime. It is only the mathematical similarity, namely phase conjugation, that brings these two devices under a common name.

SUMMARY OF THE INVENTION

The invention relates to a new method for conjugating millimeter waves, microwaves and far infrared waves. The invention further describes means for amplifying the conjugate waves.

According to the invention, a conjugated wave generator is provided for waves in the above mentioned range. This comprises means for establishing and maintaining a plasma, for establishing and maintaining therein two strong elctromagnetic waves of opposite directions of propagation and equal frequencies, said frequency being essentially equal to that of a third wave, which when directed at said plasma, generates a fourth wave which is phase conjugated respective the third wave.

According to one embodiment of the invention, the device comprises a vacuum chamber, in which high temperature gas is maintained in the state of a plasma. In a second embodiment, the device comprises solid state plasma inside a crystal, maintained by injecting dopants into said crystal.

The device comprising a plasma in a vacuum chamber, advantageously applies a magnetic field to contain the plasma, and if desired, also magnetic mirrors to slow the loss of plasma. Such a device may also act as a self exciting oscillator, if supplemented by a reflector for the electromagnetic wave emanating from the plasma. Such a reflector can be wavelength selective, thus narrowing the linewidth of the oscillator. The device then becomes a maser.

The device can be used in conjunction with an electromagnetic transmitter, tuned to the same frequency as the waves in the plasma. The reflected, phase conjugated wave, which can also be amplified, returns to the transmitter. This arrangement has many technical applications, as detailed below. The transmitter can be replaced by nuclei or electrons precessing in a magnetic field; this has its use in medicine for directing radiation into the human body in a non invasive manner.

DESCRIPTION OF THE PREFERRED EMBODIMENT

Figure 1:
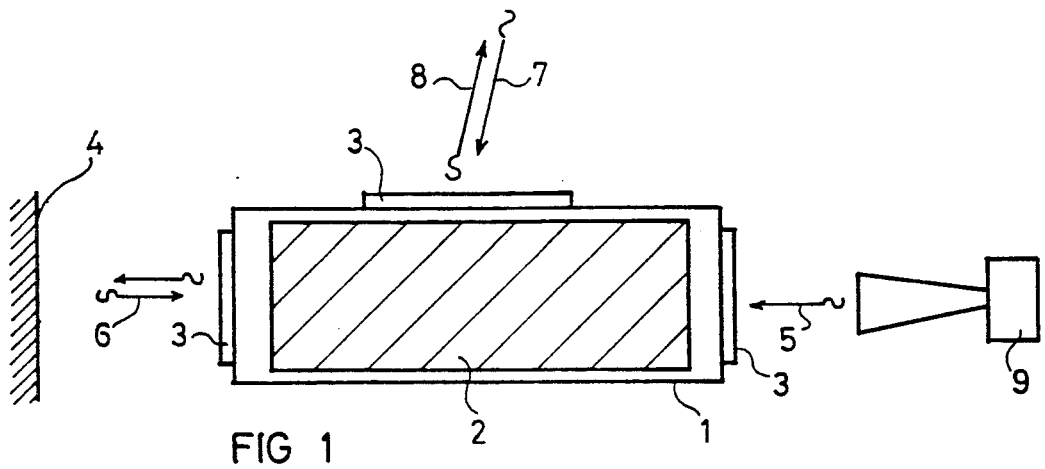
FIG. 1 show a plasma phase conjugated reflector in accordance with the invention.

It was discovered in recent years that a plasma can have very useful nonlinear properties for the generation of four-wave mixing and phase conjugation (I. Nebenzahl, A. Ron and N. Rostoker, Physical Review Letters Vol. 60 p. 1030, 1988). As a result, the plasma can conveniently be made to give rise to reflected waves of the kind discussed above, namely phase conjugated waves. For this to happen, a plasma has to be prepared with electron temperature much higher than the ion temperature, e.g. by a factor of 20. Still, the electron temperature should not be too high. A good value is 1 to 5 eV. The plasma density should preferably be in the range of $10^{-10}$ to $10^{-12}$ electrons per cc. The plasma has to be pumped by two oppositely propagating electromagnetic waves of high intensity. A good value for the intensity is 100 kWatt. Such waves are conveniently produced by radar-type magnetrons or klystrons. Alternatively, a single transmitter can be used, and the opposite wave is then produced by a reflector at the other end of the vessel.

When a third wave of nearly the same frequency enters the plasma, it interacts nonlinearly with one of the pump waves. As a result of this interaction, ion acoustic waves are produced. The second pump wave is then scattered off these ion acoustic waves and radiated out of the plasma. This radiation is phase conjugated to the above mentioned third wave. It is important to indicate that the frequency of this wave is however not identical to that of the said third wave. If the frequency of the 3rd wave is shifted by df from that of the two pump waves, then the frequency of the 4th, phase conjugated, wave is shifted by −df, i.e. in the opposite direction.

The power of the 4th wave depends linearly on the product of the powers of the two pump waves and the power of the 3rd wave. By making the power of the pump waves high enough, the 4th wave becomes stronger than that of the 3rd waves. Thus the phenomenon of phase conjugation can give rise to amplification. If now a reflector is placed outside the plasma, the outgoing wave can be sent back into the plasma, be amplified again and so on. This gives rise to a laser like buildup of oscillations, until the power in the pump waves is exhausted. In this way very powerful radiation beams can be produced, which have the directionality of the initial beam that entered the plasma vessel. This can be used, for instance, to direct microwave radiation into the body of a patient for cancer treatment. The outgoing wave can also be detected by an array of detectors, to form an image of the radiation source or of a body that has scattered the waves before entering the plasma. The said reflector can also be made wavelength selective, e.g. by a Fabry Perot arrangeent. If the combination of reflectivity and amplification is higher than unity, this arrangement will give rise to a self exciting radiation source similar to a laser but acting in the micron to centimeter regime.

The device consists of a plasma inside a vessel, a coherent radiation source, and a reflector.

The plasma can be of the hot, ionized gas type, for instance helium gas. The vessel consists of a vacuum chamber having an outer casing 1, with optionally a magnetic field in it, which can also be supplemented by magnetic mirrors at two opposite sides of the vessel along the field. The gas 2 is introduced into the vessel, the magnetic field is applied, and then the gas is ionized, e.g. by an electric discharge between an anode and a cathode at the two ends of the vessel. The plasma distributes itself along the magnetic field, mainly in the region between the magnetic mirrors. As plasma is continually lost, replenishment is assured by inflow of fresh gas into the vessel and by continuous ionization.

The vessel is provided with three ports. One Port 3 is at one end along the magnetic field. Through this port, an electromagnetic wave 5 is continually fed into the plasma. The source of this wave is a coherent oscillator such as a radio transmitter, a klystron, a magnetron, or, to achieve very high frequencies, an electron beem, modulated so as to emit high frequency waves, or a far infrared laser. At the opposite end of the vessel, a plane reflector is positioned, to reflect this wave and so produce the second pump. The reflector can consist of a metallic net of fine mesh.

Via another port 3, the 3rd wave 7 enters the vessel and wave no. 4 designated as 8 in FIG. 1 leaves it. This port is positioned on the side of the vessel, roughly at right angles to the first port.

The device as here described will hereafter be called a plasma phase conjugate reflector, or PPCR.

In another realization of the PPCR, a semiconducting crystal is loaded with dopants so as to produce a plasma of electrons and holes. To this plasma, a pump wave is applied, and when reflected from the opposite wall, the second pump wave is produced. Under these conditions, a third wave introduced into the crystal is phase-conjugate reflected as described above.

Figure 2:
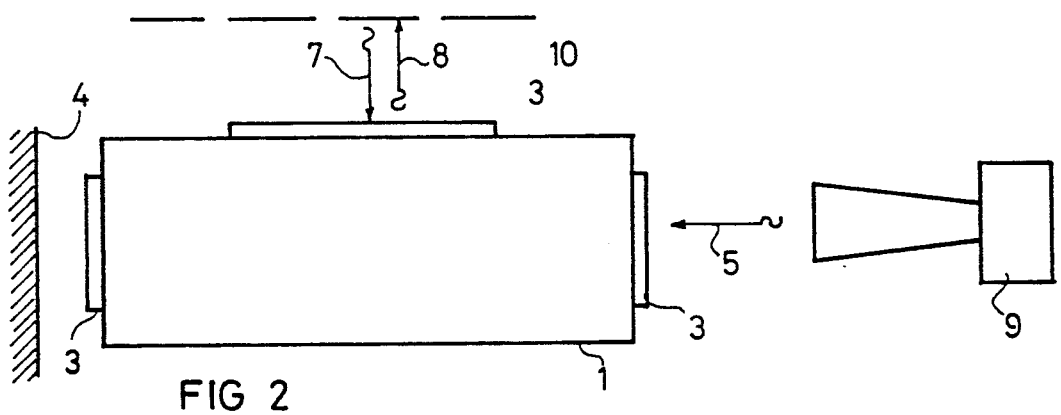
FIG. 2 shows a resonant cavity variant of the aforementioned device.

A low transmittance reflector 10 can be placed outside the vessel in front of the side port as in FIG. 2. In that case, the reflected wave is fed back into the PPCR, so that the amplification is enhanced by feedback. If the reflectivity r of the reflector and the amplification A of the PPCR combined are larger than unity, then this becomes a self exciting amplifier, or an oscillator. This oscillator is not a laser, however, since there is no significant line narrowing, because the only condition for amplification does not require L/lambda to be a whole number, as in a laser, where L is the half-path and lambda is the wavelength. However, if the single mirror is replaced by an array of two or more mirrors, constituting a Fabry Perot interferometer, the reflectivity becomes markedly wavelength dependent, and the amplification condition is then fulfilled for a narrow band only. Such a device emits directional and line narrowed emission, and is in fact a plasma laser.

Use of electromagnetic waves in the far infrared, radio, micro-, and millimeter-wave regimes is well known and widespread. However, in many applications, phase conjugate reflection can be of considerable advantage.

In the field of cancer therapy, radio waves of high frequency are aimed at a subcutaneous tumour, to cause in it a controlled temperature rise. This results in destruction of that tissue, or else enhance consumption by it of therapeutic chemicals, also aimed at its destruction or diminution.

The passage of electromagnetic radiation inside a living body is strongly influenced by local changes of the index of refraction, e.g. because of water contents variations or intrabody cavities. For this reason, the concentration of the electromagnetic radiation at the tumour is hard to achieve, and when achieved—hard to maintain as the body state and position change, e.g. as result of respiration, of movement or of digestion.

Figure 3:
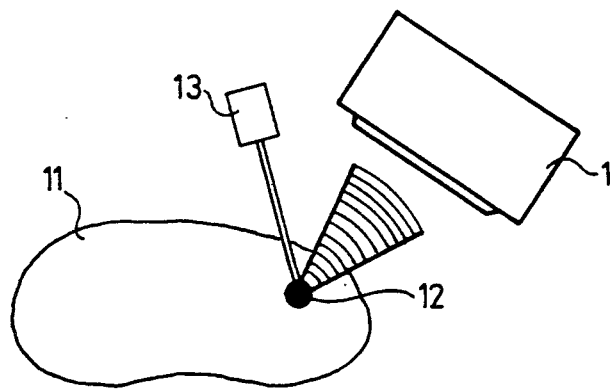
FIG. 3 shows the use of a PPCR in medical diathermy treatment of convex.

PPCR can be used to largely improve this technique. A minute RF transmitter, in the form of a syringe 13, is placed at the center of the tumour 12. A spherical electromagnetic wave spreads from this source as in FIG. 3. As the wave passes the body 11 of the treated person, the wavefront is distorted locally as a result of composition variations in the body. When the wave emerges from the patient's body, it impinges on a PPCR device shown by its casing 1, and is amplified and reflected with an inverted phase. As a result of the phase inversion, the wavefront retraces its path and converges back to the spot of its emission. Parts of the body with different indices of refraction produce phase differences along neighbouring paths from the tumour to the PPCR. These phase differences are exactly cancelled on the wave's travel back into the body. The wave then converges on the tumour, to within the diffraction limit (and to the approximation that the amplitude differences can be neglected, since PPCR can correct phase changes but not amplitude variations). This state prevails even if the patient moves or his body contents changes, because the correction via the PPCR takes place with speed near to that of light.

With the PPCR, a method can also be effected, which is completely non invasive, i.e. no material intervention is made into the patient's body. The patient is placed in a magnetic field, as in an NMR scanner. An RF signal is applied to cause an oscillation of nuclear spins in the body. This signal is then discontinued, and the measured oscillation subsides with a relaxation time T2 (C. P. Slichter: Magnetic Resonance. Harper and Row 1963). This relaxation time is different in tumour tissue than in normal tissue. If it is longer in the tumour, then after a time long compared to Tn but not Tt, where Tt and Tn are the relaxation times in the tumour and the normal tissue, respectively, the oscillation will be stronger in the tumour than in the rest of the body. The PPCR is now applied, being tuned to the magnetic resonance frequency of the body nuclei at the ambient magnetic field. The oscillation of the magnetic momenta of the nuclei of the tumour acts as a radiation source, which emerges out of the patient's body, impinges on the PPCR, and is amplified and phase conjugated. This radiation then penetrates the body, retraces its path and converges at the tumour, thus preferentially heating it up.

As another way of application, instead of turning on the PPCR after a certain time of relaxation, the PPCR can be kept on continually, but be initially out of resonance, and then brought to resonance by a change of the magnetic field. The temperature rise in the tumour can be measured in a non invasive way by measuring Tt.

If Tt is shorter than Tn, then one can proceed as follows. First, an RF signal of 90 deg in the xz plane is transmitted. Here, z is the direction of the magnetic field. Then another 90 deg signal is transmitted, at a time where most of the non-tumour nuclei are still in phase, thus returning them to z alignment, but the tumour nuclei are already out of phase because of their faster relaxation, so that those who happen to be in the yz plane are not rotated by the RF signal. Then a 180 deg RF signal in the xy plane is transmitted, to effect a photon echo. This echo will come mostly from tumour nuclei. The PPCR is tuned as above to respond at the time of this echo, so that again the tumour is preferentially radiated and heated.

In a similar way, the resonance radiation of the nuclear quadrupole moment or the electron spin (Slichter, op. cit.) can be employed to transfer energy from the PPCR to the human body.

In radar, a distant object is illuminated by a beam. The reflected beam is detected, and by analysing it the object's direction, distance and velocity are deduced. The reflected beam is sometimes weak, on the border of noise, so the detection is impaired. However, if the reflected beam is first met by a PPCR, it is then amplified and reemitted into space, converging exactly on the distant object. A second reflection from the object then results which is much stronger and can convey more information when detected. In this way, strong radar reflections can be obtained. Although thermal noise is also amplified, the phase conjugated reflection of this noise spreads in the sky and does not diminish the improved signal to noise ratio. Furthermore, a semi transparent reflector can be placed on the way of the amplified conjugated reflection of the object, to focus part of the energy at a nearby array of detectors. In this way, an image of the body can be formed, with signal to noise ratio improved over conventional imaging.

Electric power transmission from point to point is conventionally effected via electric cords. Electromagnetic transmission of the power as waves would result in large losses, as a result of the divergence of the transmitted beam. With PPCR, this can be avoided. For power to arrive at a point B from a source at A, a small transmitter is placed at B, and a large PPCR is placed at A. The small signal from B is amplified and reemitted as a wavefront which converges exactly on B. In this way, cordless power transmission can be effected. Applications can vary, from household appliances to earth spacekraft or spacekraft earth energy transfer.

A PPCR can also act as a responder. A responder is used to detect distant or lost objects, such as downed pilots in enemy territory. A PPCR is attached in advance to the person or object. When lost, a search beam is transmitted. The beam reaches the PPCR, being deflected, diffracted and distorted on its way, but the phase conjugate reflection nevertheless traces exactly the same path back and converges again at the transmitter, to within the diffraction limit. The phase conjugate reflection is then detected, thus guiding the way to the lost object or person. Of no less importance may be the fact, that the PPCR emits only in the direction of the beam impinging on it, spreading no unnecessary energy in other directions. This may be of special importance for a lost person in enemy territory, so that he would not get detected by others but friendly forces.

A hydrogen plasma was produced by the application of two plasa guns. This produced an ionized gas of density 10~11 electrons per cc. The electron temperature was 4 eV and the ion temperature less than 0.1 eV. The electron temperature was measured by launching ion acoustic wavesand detecting them at various distances. The ion temperature was measured by a velocity analysis of ion speeds.

Waves of 30 GHz frequency were produced with a magnetron and introduced into the plasma via two opposite ports. The beam intensity was 100 kWatt and the antenna diameter was 60 mm.

A weak signal was launched at right angles to the pump beams, at a freqency shifted by several MHz with a modulator. This frequency shift was adjusted until maximum phase conjugated reflection was attained. The evidence that the measured reflection is phase conjugate was obtained by the dependence of the reflected power on the square of the power of the pump wave. Amplification of up to a factor of 10 in power was obtained in this way.

I claim:

1. A method for generating conjugated waves having a frequency in the range from micrometers long to radio wavelengths, and for the amplification of said conjugated waves, which comprise the steps of establishing and maintaining in a plasma two waves of opposing directions of propagation and of essentially identical frequencies, establishing a third wave of essentially the same frequency, said third wave entering the plasma at an angle of from about 60° to 90° respective the first two waves, wherein a fourth wave which is phase conjugated respective the third wave is produced.

2. A method according to claim 1, where the plasma is a hot plasma of ionized gas.

3. A method according to claim 1, where the plasma is a solid state plasma in a crystal.

4. A device according to claim 3, comprising in addition a reflector which acts as a self-exciting oscillator.

5. A device according to claim 4, supplemented by a reflector, acting together as a self-exciting oscillator.

6. A device for generating conjugated waves comprising in combination:
   means for establishing and maintaining a plasma;
   means for establishing and maintaining in said plasma two waves of opposite directions of propagation and of essentially identical frequencies;
   means for directing a third electromagnetic wave of essentially identical wavelength at said plasma so that it will enter the plasma at a predetermined angle respective the two waves; and
   thereby generating a fourth electromagnetic wave which is phase-conjugated respective the third wave.

7. A device according to claim 6, wherein said means for establishing a plasma comprises:
   a vacuum vessel, an ionization source to produce a plasma in said vessel;
   wherein said vessel has ports to introduce electromagnetic waves, and wherein said means for directing a third electromagnetic wave is a radiation source and means for directing said third wave at the desired angle to enter the plasma, thereby resulting in the desired conjugated and amplified wave.

8. A device according to claim 6, comprising means for establishing and maintaining a magnetic field to contain the plasma, and magnetic mirrors adapted to slow the loss of plasma.

9. A device according to claim 6, where the plasma is a solid state plasma of electrons in a crystal.

10. A device according to claim 9 comprising a crystal, a current source for producing the solid state plasma, a set of high frequency leads to introduce a high amplitude wave into the crystal and another set of high frequency leads to couple the signal and reflected wave to the plasma.

11. A device according to claim 6, comprising an electromagnetic transmitter of small dimensions, that can be inserted at a desired location into a human body, which transmits at a frequency essentially identical with that fed into the plasma, thus resulting in an amplified phase conjugated wave concentrated at a small region in the human body where the transmitter is located.

12. A device according to claim 6, to be used in combination with a magnetic field of a large volume, into which a human body or part thereof can be placed, and a high frequency transmitter tuned in such a manner as to cause nuclei or electrons in the human body to precess in said magnetic field, means for operating said device at desired time intervals, so that after a certain predetermined period of time the nuclei of a tumor in said human body will precess about the magnetic field and emit a signal which is then amplified and conjugated by the plasma so that radiation is concentrated at the tumor site, so as to increase its temperature.

13. A device according to claim 6, in combination with a radar ray source to illuminated distant objects, so that the radar ray reflected from such an object enters the device and an amplified phase conjugated ray is then emitted and directed at the distant object, the frequency of the radar ray being near the frequency of the strong electromagnetic waves fed into the plasma.

14. A device according to claim 13, comprising a semitransparent reflector, so that the phase conjugated ray is focused in an image plane to form a radar image of the distant object.

15. A device according to claim 6, in combination with an electromagnetic wave transmitter, so that when the transmitter radiates toward the plasma at low intensity, a phase conjugated wave of high intensity is emitted by the plasma and concentrated in the vicinity of the transmitter, and is then converted into electric power.

16. A device according to claim 6, in combination with a strong transmitter, so that a person or an object attached to the device can be traced or found by a person operating the transmitter, using the radiation originating in the transmitter, amplified by the device, and sent back to the transmitter.

17. A device according to claim 6, wherein the plasma is a solid state plasma of holes in a crystal.

18. A device according to claim 6, wherein the plasma is a solid state plasma of holes and electrons in a crystal.

* * * * *